(12) United States Patent
Kim et al.

(10) Patent No.: US 10,124,316 B2
(45) Date of Patent: *Nov. 13, 2018

(54) SUPER ABSORBENT RESIN FOR ABSORBING BLOOD OR HIGH VISCOSITY LIQUID AND METHOD FOR PREPARING SAME

(71) Applicant: LG Chem, Ltd., Seoul (KR)

(72) Inventors: Young-Sam Kim, Daejeon (KR); Yeon-Woo Hong, Daejeon (KR); Dong-Jo Ryu, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/319,048

(22) PCT Filed: Dec. 14, 2015

(86) PCT No.: PCT/KR2015/013687
§ 371 (c)(1),
(2) Date: Dec. 15, 2016

(87) PCT Pub. No.: WO2016/099103
PCT Pub. Date: Jun. 23, 2016

(65) Prior Publication Data
US 2017/0144130 A1    May 25, 2017

(30) Foreign Application Priority Data
Dec. 18, 2014 (KR) .......................... 10-2014-0183228

(51) Int. Cl.
| | | |
|---|---|---|
| *A61L 15/24* | (2006.01) | |
| *B01J 20/26* | (2006.01) | |
| *A61F 13/53* | (2006.01) | |
| *B01J 20/30* | (2006.01) | |
| *C08F 220/06* | (2006.01) | |
| *C08F 220/28* | (2006.01) | |
| *A61L 15/60* | (2006.01) | |
| *C08J 3/12* | (2006.01) | |

(52) U.S. Cl.
CPC ............. *B01J 20/265* (2013.01); *A61F 13/53* (2013.01); *A61L 15/24* (2013.01); *A61L 15/60* (2013.01); *B01J 20/3085* (2013.01); *C08F 220/06* (2013.01); *C08F 220/28* (2013.01); *C08J 3/126* (2013.01); *C08F 2220/282* (2013.01); *C08J 2333/02* (2013.01); *C08J 2433/14* (2013.01)

(58) Field of Classification Search
CPC .. B01L 20/265; B01L 20/3085; C08F 220/06; C08F 220/28; C08F 2220/282; B01J 20/3085; A61L 15/24
See application file for complete search history.

(56) References Cited

U.S. PATENT DOCUMENTS

| | | |
|---|---|---|
| 5,998,032 A | 12/1999 | Hansen et al. |
| 6,395,395 B1 | 5/2002 | Hansen et al. |
| 6,627,249 B2 | 9/2003 | Hansen et al. |
| 2002/0164375 A1 | 11/2002 | Hansen et al. |
| 2008/0021130 A1* | 1/2008 | McIntosh et al. ....... C08L 51/06 523/111 |
| 2008/0032888 A1 | 2/2008 | Nakamura et al. |
| 2013/0324396 A1 | 12/2013 | Honda et al. |
| 2014/0058048 A1* | 2/2014 | Won et al. .............. B01J 20/267 525/384 |
| 2014/0316040 A1* | 10/2014 | Shi et al. ................. A61L 15/60 524/320 |
| 2015/0197587 A1 | 7/2015 | Lee et al. |
| 2015/0259522 A1 | 9/2015 | Lee et al. |
| 2017/0095792 A1* | 4/2017 | Kim et al. ............. B01J 20/265 |
| 2017/0114192 A1* | 4/2017 | Kim et al. ............... C08J 3/245 |

FOREIGN PATENT DOCUMENTS

| | | |
|---|---|---|
| JP | H06313042 A | 11/1994 |
| JP | H06313043 A | 11/1994 |
| JP | H06313044 A | 11/1994 |
| JP | H08143782 A | 6/1996 |
| JP | H09241322 A | 9/1997 |
| JP | 2002105125 A | 4/2002 |
| KR | 10-0330127 B1 | 3/2002 |
| KR | 20070012731 A | 1/2007 |
| KR | 20140063457 A | 5/2014 |
| WO | 2012132861 A1 | 10/2012 |
| WO | 2014077516 A1 | 5/2014 |
| WO | 20150108472 A1 | 7/2015 |

OTHER PUBLICATIONS

International Search Report from PCT/KR2015/013687, dated Mar. 28, 2016.
Third Party Observation for PCT/KR2015/013687 dated Apr. 18, 2017.

* cited by examiner

*Primary Examiner* — Nathan M Nutter
(74) *Attorney, Agent, or Firm* — Lerner, David, Littenberg, Krumholz & Mentlik, LLP

(57) ABSTRACT

Disclosed herein is a superabsorbent polymer with a surface modified with both a polyvalent cationic salt and a polycarbonic acid-based copolymer, which is able to effectively absorb blood or highly viscous liquid, and a method for preparing the same.

14 Claims, 2 Drawing Sheets

US 10,124,316 B2

SUPER ABSORBENT RESIN FOR ABSORBING BLOOD OR HIGH VISCOSITY LIQUID AND METHOD FOR PREPARING SAME

CROSS REFERENCE TO RELATED APPLICATIONS

The present application is a national phase entry under 35 U.S.C. § 371 of International Application No. PCT/KR2015/013687 filed Dec. 14, 2015, which claims priority from Korean Patent Application No. 10-2014-0183228, filed on Dec. 18, 2014, which are hereby incorporated by reference herein.

TECHNICAL FIELD

The present disclosure relates to a superabsorbent polymer for absorbing blood or highly viscous liquid, and to a method for preparing the same. More particularly, the present disclosure relates to a superabsorbent polymer having a surface modified with both a polyvalent cationic salt and a polycarbonic acid-based copolymer, which is able to effectively absorb blood or highly viscous liquid, and a method for preparing the same.

BACKGROUND ART

Superabsorbent polymers (SAPs) are synthetic polymer materials having a capacity to absorb 500 to 1000 times their own weight in moisture. Although developed for practical use in sanitary items, SAPs now find additional applications in a variety of fields including as disposable diapers for children, sanitary pads, raw materials in soil conditioners for horticulture, water stopping agents for civil engineering and construction applications, sheets for raising seedlings, freshness preservatives for food distribution, goods for fomentation, and the like.

In practice, however, SAPs are now used, for the most part, for diapers for urine absorption, but not in sanitary pads for women because urine and menstrual blood are quite different from each other as to the physical properties thereof. Containing salts, proteins and cells as well as water, menstrual blood is so highly viscous that it does not readily diffuse. In addition, large cell masses are not absorbed into SAPs, but form a film on the surface, which serves as a barrier to the absorption of blood. For these reasons, SAPs are used only in small amounts in sanitary pads. Thus, there is a need for a novel approach to the development of SAPs exhibiting improved blood absorption.

DISCLOSURE

Technical Problem

Leading to the present disclosure, intensive and thorough research into SAPs resulted in the finding that SAPs, when the surface thereof is modified with a water-soluble polyvalent cationic salt and a polycarbonic acid-based copolymer, improve in physical properties, including blood fluidity, as analyzed by a new assay for measuring the weight of an SAP coagulated with clotted blood or highly viscous liquid. It is therefore an object of the present disclosure to provide a superabsorbent polymer that is improved in blood fluidity so that it is suitable for use in sanitary pads, and a method for preparing the same.

Technical Solution

In order to accomplish the above object, an aspect of the present disclosure provides a superabsorbent polymer for absorbing blood or highly viscous liquid, wherein the surface of the superabsorbent polymer is modified with a water-soluble polyvalent cationic salt and a polycarbonic acid-based copolymer.

Another aspect of the present disclosure provides a method for preparing a surface-modified superabsorbent polymer, comprising:

a) providing a superabsorbent polymer;

b) pre-treating the superabsorbent polymer of step a) by mixing a water-soluble polyvalent cationic salt in an amount of 0.001 to 5.0 parts by weight, based on 100 parts by weight of the superabsorbent polymer provided in step a); and c) surface treating the pre-treated superabsorbent polymer of step b) by mixing a polycarbonic acid-based copolymer in an amount of 0.001 to 5.0 parts by weight, based on 100 parts by weight of the superabsorbent polymer provided in step a).

Advantageous Effects

Compared to conventional SAPs, the SAPs prepared by surface modification with a water-soluble polyvalent cationic salt and a polycarbonic acid-based copolymer in accordance with the present disclosure are greatly improved in blood fluidity as analyzed by a new assay, proposed in the present disclosure, for measuring the weight of an SAP coagulated with clotted blood or highly viscous liquid. Thus, the SAPs of the present disclosure enjoy the advantage of blood fluidity that is sufficiently improved to make them suitable for use in sanitary pads for absorbing blood or highly viscous liquid.

BEST MODE

Below, a detailed description will be given of the present disclosure.

In accordance with an aspect thereof, the present disclosure addresses a superabsorbent polymer for absorbing blood or highly viscous liquid, wherein the surface of the superabsorbent polymer is modified with a water-soluble polyvalent cationic salt and a polycarbonic acid-based copolymer.

In one embodiment, the superabsorbent polymer may be a superabsorbent polymer product or a superabsorbent base resin. Particularly, a superabsorbent base resin, which is not yet surface crosslinked, was found to greatly improve in blood fluidity after the surface modification of the present disclosure. Conventionally, superabsorbent polymer products have been used in diapers that allow one to defecate or urinate, but a superabsorbent polymer base resin that is not yet surface crosslinked has been found to be applicable to blood absorption after the surface modification according to the present disclosure, which leads to the present invention.

The water-soluble polyvalent cationic salt plays a role in surface crosslinking in the superabsorbent polymer. In some embodiments, the water-soluble polyvalent cationic salt may be used in an amount of 0.001 to 5.0 parts by weight, based on 100 parts by weight of the superabsorbent polymer. Within this content range, the water-soluble polyvalent cationic salt allows the superabsorbent polymer to increase in permeability without causing a significant degradation of other properties.

In the water-soluble salt, the polyvalent cationic ion may be selected from the group consisting of $Al^{3+}$, $Zr^{4+}$, $Sc^{3+}$, $Ti^{4+}$, $V^{5+}$, $CR^{3+}$, $Mn^{2+}$, $Fe^{3+}$, $Ni^{2+}$, $Cu^{2+}$, $Zn^{2+}$, $Ag^+$, $Pt^{4+}$, $Au^+$, and a combination thereof while the counterpart anion may be selected from the group consisting of sulfate ($SO_4^{2-}$), sulfite ($SO_3^{2-}$), nitrate ($NO^{3-}$), metaphosphate ($PO^{3-}$), phosphate ($PO_4^{3-}$), and a combination thereof. The water-soluble salt may be particularly aluminum sulfate ($Zr(SO_4)_2$), and more particularly zirconium sulfate ($Zr(SO_4)_2$), and may be in the form of a hydrate.

Figure 3:
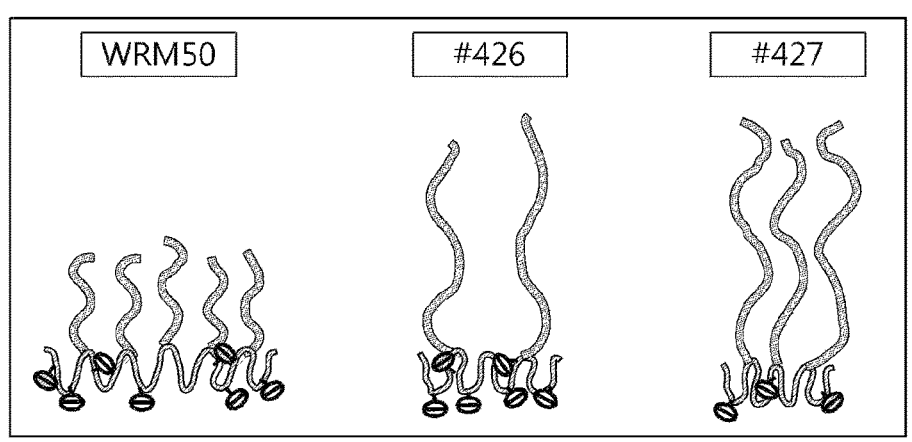
FIG. 3 is a schematic diagram showing the chemical structures of polycarbonic acid-based copolymers WRM50, #426, and #427.

The polycarbonic acid-based copolymer may act as a superplasticizer in the superabsorbent polymer, and has a structure in which a main chain is conjugated with a plurality of side chains or branches, like a comb, as shown in FIG. 3.

According to some embodiments, the polycarbonic acid-based copolymer consists of a main chain having a (meth)acrylic acid-based monomer as a structural unit; and a side chain composed of an alkoxypolyalkylene glycol mono(meth)acrylic acid ester monomer. Preferably, the polycarbonic acid-based copolymer is contained in an amount of 0.001 to 5.0 parts by weight, based on 100 parts by weight of the superabsorbent polymer. When used after treatment of the superabsorbent polymer with the water-soluble polyvalent cationic salt, the polycarbonic acid-based copolymer in this content range can allow the superabsorbent polymer to improve in permeability while still retaining high processability, and without a significant degradation of other properties.

In a particular embodiment, the polycarbonic acid-based copolymer may contain 50 to 99% by weight of the alkoxypolyalkylene glycol mono(meth)acrylic acid ester monomer and 1 to 50% by weight of the (meth)acrylic acid monomer.

With the monomers in these ranges, the copolymer is advantageous in imparting excellent dispersibility, slump retention, and initial dispersibility, as well as in expressing appropriate air entrainment.

The alkoxypolyalkylene glycol mono(meth)acrylic acid ester monomer that serves as a side chain of the polycarbonic acid-based copolymer may be represented by the following Chemical Formula 1:

[Chemical Formula 1]

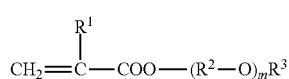

wherein,
$R^1$ is a hydrogen atom or methyl;

$R^2O$ represents an oxyalkylene moiety of 2 to 4 carbon atoms;
$R^3$ is alkyl of 1 to 4 carbon atoms; and
m is an integer of 50 to 200, expressing an average addition mole number of oxyalkylene.

When the average addition mole number of oxyalkylene ranges from 50 to 200, the side chain guarantees excellent dispersibility and slump retention. In a particular embodiment, the average addition mole number of oxyalkylene may be between 50 to 150.

The alkoxy polyalkylene glycol mono(meth)acrylic acid ester monomer may be at least one selected from the group consisting of methoxypolyethylene glycol mono(meth)acrylate, methoxypolypropylene glycol mono(meth)acrylate, methoxypolybutylene glycol mono(meth)acrylate, methoxypolyethylene glycol polypropylene glycol mono(meth)acrylate, methoxypolyethylene glycol polybutylene glycol mono(meth)acrylate, methoxypolypropylene glycol polybutylene glycol mono(meth)acrylate, methoxypolyethylene glycol polypropylene glycol polybutylene glycol mono(meth)acrylate, ethoxypolyethylene glycol mono(meth)acrylate, ethoxypolypropylene glycol mono(meth)acrylate, ethoxypolybutylene glycol mono(meth)acrylate, ethoxypolyethylene glycol polypropylene glycol mono(meth)acrylate, ethoxypolyethylene glycol polybutylene glycol mono(meth)acrylate, ethoxypolypropylene glycol polybutylene glycol mono(meth)acrylate, and ethoxypolyethylene glycol polypropylene glycol polybutylene glycol mono(meth)acrylate.

The (meth)acrylic acid monomer that serves as a structural unit of the main chain of the polycarbonic acid-based copolymer may be represented by the following Chemical Formula 2:

$$R^2\text{—}COOM^1 \qquad \text{[Chemical Formula 2]}$$

wherein,
$R^2$ is an unsaturated hydrocarbon of 2 to 5 carbon atoms; and
$M^1$ is a hydrogen atom, a monovalent or divalent metal, an ammonium group, or an organic amine group.

The (meth)acrylic acid monomer of Chemical Formula 2 may be at least one selected from the group consisting of an acrylic acid, a methacrylic acid, a monovalent or divalent metal salt thereof, an ammonium salt thereof, and an organic amine salt thereof.

The polycarbonic acid-based copolymer may be prepared by copolymerizing the monomers in the presence of a polymerization initiator. Copolymerization may be carried out by solution polymerization or bulk polymerization, but is not limited thereto.

For example, when polymerization is performed with water as a solvent, a water-soluble polymerization initiator, such as ammonium, alkali metal persulfate, or hydrogen peroxide may be employed. Solution polymerization in a solvent such as a lower alcohol, an aromatic hydrocarbon, an aliphatic hydrocarbon, an ester compound or a ketone compound may employ as a polymerization initiator a peroxide, such as benzoylperoxide, lauroylperoxide, or cumen hydroperoxide, or an aromatic azo compound such as azobisisobutyronitrile. In this regard, an accelerator such as an amine compound may be used in combination therewith.

For polymerization in a water-lower alcohol mixture solvent, an eligible combination of the various polymerization initiators, and optionally the accelerator, may be used.

The polymerization initiator may be used in an amount of 0.5% to 5% by weight, based on the total weight of the monomer mixture employed, while the polymerization temperature may be set depending on the kind of the solvent or the polymerization initiator, and may range from 0° C. to 120° C.

In order to control the molecular weight of the polycarbonic acid-based copolymer, a thiol-based chain transfer agent may be added. The thiol-based chain transfer agent may be at least one selected from the group consisting of mercapto ethanol, thioglycerol, thioglycolic acid, 2-mercapto propionic acid, 3-mercapto propionic acid, thiomalic acid, thioglycolic acid octyl, and 3-mercapto propionic acid octyl, and may be used in an amount of 0.01% to 5% by weight, based on the total weight of the monomer mixture.

In a particular embodiment, the polycarbonic acid-based copolymer or a neutralized salt thereof may range in weight average molecular weight from 30,000 to 70,000, and preferably from 40,000 to 60,000 in consideration of dispersibility, as measured by GPC (Gel Permeation Chromatography).

In some embodiments of the present disclosure, #427 polycarbonic acid-based copolymer, a novel polymer derived from the commercially available polycarbonic acid-based copolymer WRM 50 (LG Chem) by alteration of the side chain length and chain density thereof, is used for the surface modification leading to an improvement in blood fluidity as analyzed by a new assay, proposed by the present disclosure, for measuring the weight of the SAP coagulated with clotted blood or highly viscous liquid. For reference, #427 is identical to WRM50, with the exception that the molecular weight (length) of the alkoxypolyalkylene glycol mono(meth)acrylic acid ester monomer, a side chain, is changed.

In Table 1, below, the basic properties of the polycarbonic acid-based copolymers WRM50, #426, and #427 are described, including TSC (Total solid content: %), pH, and viscosity (25° C.), and the results of GPC analysis are also listed. In addition, as shown in FIG. 3 and Table 2, the polycarbonic acid-based copolymers differ in structural features from one another. The side chain alkoxypolyalkylene glycol mono(meth)acrylic acid ester monomer is longer (heavier) in #426 and #427 than WRM50, with a higher density of the side chain for #427 than #426.

TABLE 1

Properties of Three PCEs WRM50, #426, and #427

Basic Properties

|  | TSC(%) | pH | Vis.(25° C.) |
|---|---|---|---|
| WRM50 | 50.34 | 4.9 | 334 |
| #426 | 44.71 | 5.06 | 307 |
| #427 | 44.12 | 4.88 | 204 |

GPC Results

| Sample | Mw | PDI | Low-Mw (%) |
|---|---|---|---|
| WRM50 | 40,654 | 1.94 | 17.7 |
| #426 | 27,780 | 2.18 | 4.2 |
| #427 | 16,911 | 1.81 | 5.9 |

TABLE 2

| Polymer | Perfomance | Main Chain | Side Chain | Density of side chain |
|---|---|---|---|---|
| WRM50 | Low dispersion Low retention | Long | Short | High |
| #426 | High dispersion | Short | Long | Low |
| #427 | High dispersion High retention | Very short | Long | High |

In some embodiments of the present disclosure, #427 polycarbonic acid-based copolymer, a novel polymer derived from the commercially available polycarbonic acid-based copolymer WRM 50 (LG Chem) by modification of the side chain length and chain density thereof, is used for surface modification of the superabsorbent polymer, which leads to an improvement in blood fluidity as analyzed by a new assay, proposed in the present disclosure, for measuring the weight of an SAP coagulated with clotted blood or highly viscous liquid.

The SAPs that are surface-modified according to the present disclosure were observed to improve in properties related to blood absorption. In the present disclosure, an assay for measuring blood absorption-related properties is proposed before the surface modification of the SAPs. Among typical assays for measuring physical properties is centrifugal retention capacity (capacity for retaining water). However, centrifugal retention capacity is performed for saline. Thus, a new assay should be proposed for testing SAPs for the ability to absorb blood thereinto and to spread blood thereover. In some embodiments of the present disclosure, the surface modification of a superabsorbent polymer is performed by evenly applying an aqueous polyvalent cationic salt solution (e.g., aluminum sulfate) and an aqueous polycarbonic acid-based copolymer solution to the surface of the superabsorbent polymer with the aid of a high-speed mixer. The sample, surface-treated with a polyvalent cationic salt and then with a polycarbonic acid-based copolymer, was found to further absorb and spread blood thereonto than conventional SAPs or samples obtained through surface modification with either a polyvalent carbonic salt or a polycarbonic acid-based copolymer, as measured by the new assay. Also, the ability of SAPs to absorb and spread blood was found to vary depending on the length and density of the branch of the polycarbonic acid-based copolymer.

In the blood test proposed according to the present disclosure, the superabsorbent polymer for absorbing blood or highly viscous liquid can be assayed for blood fluidity by measuring the weight of the superabsorbent polymer, coagulated with clotted blood or highly viscous liquid, after 0.1 mg of blood or highly viscous liquid is dropped on 1 g of the superabsorbent polymer. Particularly, a superabsorbent base resin, after modification with both the water-soluble polyvalent cationic salt and the polycarbonic acid-based copolymer, was observed to improve greatly in blood fluidity compared to conventional SAPs. The blood test is adapted to calculate blood fluidity by adding blood dropwise onto a superabsorbent polymer to clot the blood, and measuring the weight of the superabsorbent polymer coagulated with the clotted blood.

The superabsorbent polymer product useful in the present disclosure is prepared by a method comprising:

a) polymerizing a monomer composition containing a water-soluble ethylenically unsaturated monomer and a polymerization initiator using heat or light to give a hydrogel phase polymer;

b) drying the hydrogel phase polymer;

c) milling the dried hydrogel phase polymer into superabsorbent polymer particles; and d) adding a surface cross-linking agent to the milled superabsorbent polymer particles to perform a surface cross-linking reaction.

The superabsorbent base resin is prepared by a method comprising:

a) polymerizing a monomer composition, containing a water-soluble ethylenically unsaturated monomer and a polymerization initiator, using heat or light to give a hydrogel phase polymer;

b) drying the hydrogel phase polymer; and c) milling the dried hydrogel phase polymer into superabsorbent polymer particles.

As used herein, the term "superabsorbent base resin" refers to particles obtained by drying and milling the hydrogel phase polymer. In greater detail, the hydrogel phase polymer has the form of a jelly 1 cm or larger in size with a high water content (50% or higher) after the completion of polymerization, and is dried and milled into a powder. That is, the superabsorbent base resin is a pre-crosslinking superabsorbent polymer, and thus the hydrogel phase polymer corresponds to a product in a meso-phase of the method.

The preparation of a superabsorbent polymer product or a superabsorbent base resin in accordance with the present disclosure starts with a) thermal polymerization or photopolymerization of water-soluble, ethylenically unsaturated monomers into a hydrogel phase polymer in the presence of a polymerization initiator.

For this, steps or processes typical in the art may be employed. In detail, the polymerization initiator contained in the monomer composition for use in the preparation of the superabsorbent polymer product or the superabsorbent base resin of the present disclosure may depend on the type of polymerization. That is, either a photopolymerization initiator or a thermal polymerization initiator may be used. For photopolymerization, however, heat is generated not only through UV light irradiation, but also through the polymerization, which is an exothermic reaction. Hence, a thermal polymerization initiator may be additionally contained, even upon photopolymerization.

Although no special limitations are imposed thereon, the thermal polymerization initiator useful in the method for the preparation of the superabsorbent polymer product or the superabsorbent base resin according to the present disclosure may be preferably selected from the group consisting of a persulfate salt, an azo compound, hydrogen peroxide, ascorbic acid, and a combination thereof. Examples of the persulfate initiator include sodium persulfate ($Na_2S_2O_8$), potassium persulfate ($K_2S_2O_8$), and ammonium persulfate (($NH_4)_2S_2O_8$). Among the azo compounds useful as a thermal polymerization initiator in the preparation of the superabsorbent polymer product or the superabsorbent base resin according to the present disclosure are 2,2-azobis(2-amidinopropane) dihydrochloride, 2,2-azobis-(N,N-dimethylene) isobutyramidine dihydrochloride, 2-(carbamoylazo)isobutyronitrile, 2,2-azobis[2-(2-imidazolin-2-yl)propane] dihydrochloride, and 4,4-azobis-(4-cyanovaleric acid).

The photopolymerization initiator available in the method for the preparation of the superabsorbent polymer product or the superabsorbent base resin according to the present disclosure, although not specifically limited, may be preferably selected from the group consisting of benzoin ether, dialkyl acetophenone, hydroxyl alkylketone, phenyl glyoxylate, benzyl dimethyl ketal, acyl phosphine, α-aminoketone, and a combination thereof. As an acyl phosphine, commercially available Lucirin TPO, that is, 2,4,6-trimethyl-benzoyl-trimethyl phosphine oxide, may be used.

So long as it is typically used in the preparation of SAPs, any water-soluble, ethylenically unsaturated monomer may be used without limitation in the method of preparing the superabsorbent polymer product or the superabsorbent base resin according to the present disclosure. Preferably, the water-soluble, ethylenically unsaturated monomer may be selected from the group consisting of an anionic monomer or a salt thereof, a non-ionic hydrophilic monomer, an amino group-containing unsaturated monomer and a quaternary salt thereof, and a combination thereof. Examples of the water-soluble, ethylenically unsaturated monomer include anionic monomers or salts thereof, such as acrylic acid, methacrylic acid, anhydrous maleic acid, fumaric acid, crotonic acid, itaconic acid, 2-acryloylethanesulfonic acid, 2-methacryloylethanesulfonic acid, 2-(meth)acryloylpropanesulfonic acid, and 2-(meth)acrylamide-2-methylpropane sulfonic acid; non-ionic hydrophilic monomers, such as (meth)acrylamide, N-substituted (meth)acrylate, 2-hydroxyethyl (meth)acrylate, 2-hydroxypropyl (meth)acrylate, methoxypolyethylene glycol (meth)acrylate, and polyethylene glycol (meth)acrylate; and an amino group-containing unsaturated monomers or quaternary salts thereof, such as (N,N)-dimethylaminoethyl (meth)acrylate and (N,N)-dimethylaminopropyl (meth)acrylamide, with preference for an acrylic acid or a salt thereof. SAPs that are particularly improved in absorbency can be advantageously obtained from acrylic acid or a salt thereof.

For resource recycling, micro- or submicro-particles of the prepared SAPs, that is, the prepared superabsorbent polymer product or superabsorbent base resin with a particle size of less than 150 μm, may be contained in the monomer composition during the preparation of the superabsorbent polymer product or the superabsorbent base resin according to the present disclosure. In detail, polymer particles having a particle size of less than 150 μm may be added to the monomer composition before the polymerization reaction or to the reaction mixture at an initial, middle, or late phase of the polymerization. No limitations are imparted as to the amount of the superabsorbent polymer powder. Preferably, it is added in an amount of 1 to 10 parts by weight, based on 100 parts by weight of the monomer composition, in terms of preventing physical properties of the final SAPs from deteriorating.

In the method for preparing a superabsorbent polymer product or a superabsorbent base resin in accordance with the present disclosure, the content of the water-soluble ethylenically unsaturated monomer in the monomer composition may be suitably determined in consideration of the polymerization time and reaction conditions, and may preferably range from 40 to 55% by weight. Less than 40% by weight of the water-soluble ethylenically unsaturated monomer is economically disadvantageous. On the other hand, when the monomer is used in an amount exceeding 55% by weight, the resulting hydrogel phase polymer may be milled at a low rate.

So long as it is typically used for thermal polymerization or photopolymerization in the art, any technique may be applied, without limitation, to the preparation of a hydrogel phase polymer from the monomer composition. Polymerization is broadly divided into thermal polymerization and photopolymerization according to the energy source. In general, thermal polymerization may be performed in a reactor installed with a stirring shaft, such as a kneader. For photopolymerization, a conveyer belt may run under a light source in a reactor. These techniques are illustrated as exemplary embodiments, but are not to be construed to limit the present disclosure.

For example, a hydrogel phase polymer is prepared in a reactor installed with a stirring shaft, such as a kneader, through thermal polymerization, e.g., by providing hot air to the reactor or by heating the reactor, and is discharged from the reactor as particles millimeters to centimeters long according to the type of the stirring shaft. In detail, the size of the obtained hydrogel phase polymer particles may vary depending on the concentration and feeding rate of the monomer composition, and typically ranges from 2 to 50 mm.

In addition, when photopolymerization is performed on a movable conveyer belt, as mentioned above, the resulting hydrogel phase polymer may typically take the form of a sheet having a width equal to that of the belt. The thickness of the polymer sheet may vary depending on the concentration and feeding rate of the monomer composition. The monomer composition is preferably fed such that a sheet-like polymer having a thickness of 0.5 to 5 cm may be obtained. A feeding condition of the monomer composition that affords too thin a polymer sheet may result in low productivity. In contrast, when the thickness of the sheet-like polymer exceeds 5 cm, the polymerization reaction may not occur evenly throughout the entire thickness.

The light source available in the photopolymerization step does not have any special limitations imposed thereon. Any UV light that causes a photopolymerization reaction may be employed. For example, light with a wavelength of 200 to 400 nm, or a UV light source such as that from a Xe lamp, a mercury lamp, or a metal halide lamp, may be used. The photopolymerization may be performed for approximately 5 sec to approximately 10 min under a light intensity of approximately 0.1 mw/cm$^2$ to approximately 1 kw/cm$^2$. When the light intensity is too low or the irradiation time is too short, the polymerization reactions may be insufficient. On the other hand, too high a light intensity or too long an irradiation time may deteriorate the quality of the superabsorbent polymers.

Next, step b) of drying the hydrogel phase polymer is carried out in the method for preparing a superabsorbent polymer product or a superabsorbent base resin in accordance with the present disclosure.

The hydrogel phase polymer obtained in step a) has a water content of 30 to 60% by weight. As used herein, the term "water content" refers to the weight percentage of water to the total weight of the hydrogel phase polymer. The amount of water may be obtained by subtracting the weight of dried polymer from the total weight of the hydrogel phase polymer. (In detail, after the polymer is dried by infrared heating, the mass loss attributed to moisture evaporation is measured. The drying conditions are such that the atmosphere is heated from room temperature to 180° C. and maintained at 180° C., with a total drying time set to 20 min, including 5 min for the temperature increase.)

The hydrogel phase polymer obtained in step a) is subjected to a drying process. Preferably, the drying may be conducted at 150° C. to 250° C. The term "drying temperature", as used herein, means the temperature of a heat medium provided for drying or the temperature of a dryer including a heat medium and the polymer therein.

A drying temperature of less than 150° C. may make the drying time long, and is liable to degrade the properties of the final SAPs. When the drying temperature exceeds 250° C., there is a high likelihood that only the surface of the polymer will be dried, which leads to the generation of overly fine powder in a subsequent milling step, and the degradation of the properties of the final SAPs. Preferably, the drying may be conducted at 150° C. to 250° C., and more particularly at 160° C. to 200° C.

The drying time is not specifically limited, and may be set to range from 20 to 90 min in consideration of process efficiency.

Any drying process that is typically used to dry hydrogel phase polymers may be selected, without limitation as to the configuration thereof. In detail, the drying step may be conducted by supplying hot air, or irradiating with IR light, microwaves, or UV light. After the drying step, the water content of the polymer may be decreased to 0.1 to 10% by weight.

In advance of the drying step, as needed, the method for preparing SAPs in accordance with the present disclosure may further comprise briefly crushing the hydrogel phase polymer to enhance the efficiency of the drying step. In this brief crushing step, the hydrogel phase polymer may be crushed into particles having a size of 1 mm to 15 mm. It is technically difficult to crush the polymer into particles smaller than 1 mm due to the high water content of the hydrogel phase polymer. Even if it were possible to crush the polymer into particles less than 1 mm in size, the crushed particles would be prone to agglomeration. On the other hand, crushed particles having a size of greater than 15 mm do not guarantee that the subsequent drying step will be sufficient.

For use in the brief crushing step prior to the drying step, a crushing machine may be employed without limitation as to the configuration thereof. Examples of the crushing machine include, but are not limited to, a vertical pulverizer, a turbo cutter, a turbo grinder, a rotary cutter mill, a cutter mill, a disc mill, a shred crusher, a crusher, a chopper, and a disc cutter.

When a crushing step is carried out to enhance the drying efficiency in the subsequent drying step, the hydrogel phase polymer may be likely to adhere to the surface of the crusher due to its high water content. To increase the efficiency of the pre-drying crushing step, an additive that prevents the adherence of the hydrogel phase polymer to the crusher may be employed. Examples of the additive available for preventing the adherence include a powder aggregation preventer such as steam, water, a surfactant, or inorganic powder, e.g., clay or silica; a thermal polymerization initiator, such as a persulfate initiator, an azo-type initiator, hydrogen peroxide, and ascorbic acid; a crosslinking agent, such as an epoxy-based crosslinking agent, a diol-containing crosslinking agent, a crosslinking agent containing a multifunctional acrylate, e.g. a bi- or tri-functional acrylate, and a monofunctional compound containing a hydroxide group, but are not limited thereto.

After the drying step, the method for preparing a superabsorbent polymer product or a superabsorbent base resin according to the present disclosure proceeds to c) milling the dried hydrogel phase polymer into particles. The polymer particles obtained in the milling step have a particle size of 150 to 850 μm. The milling step of the method for preparing a superabsorbent polymer product or a superabsorbent base resin according to the present disclosure may be achieved with a mill, examples of which include, but are not limited to, a pin mill, a hammer mill, a screw mill, a roll mill, a disc mill and a jog mill.

For a superabsorbent polymer product, the method may further comprise d) adding a surface crosslinking agent to the milled hydrogel phase polymer to perform a surface crosslinking reaction. The surface crosslinking agents added to the superabsorbent polymer particles may have the same composition, irrespective of particle sizes, or may, as needed, be different in particle size composition.

Any surface crosslinking agent that reacts with a functional group of the polymer can be employed without limitation as to the configuration thereof in the method for preparing SAPs according to the present disclosure. Preferably to enhance properties of the SAPs thus prepared, the surface crosslinking agent may be selected from the group consisting of a polyhydric compound, an epoxy compound, a polyamine compound, a haloepoxy compound, a haloepoxy compound condensate, an oxazoline compound, a mono-, di- or polyoxazolidinone compound, a cyclic urea compound, an alkylene carbonate compound, and a combination thereof.

Concrete examples of the polyhydric alcohol compound include mono-, di-, tri-, tetra- or polyethylene glycol, monopropylene glycol, 1,3-propanediol, dipropylene glycol, 2,3,4-trimethyl-1,3-pentanediol, polypropylene glycol, glycerol, polyglycerol, 2-butene-1,4-diol, 1,4-butanediol, 1,3-butanediol, 1,5-pentanediol, 1,6-hexanediol, and 1,2-cyclohexanedimethanol.

The epoxy compound may be ethylene glycol diglycidyl ether or glycidol. The polyamine compound may be selected from the group consisting of ethylene diamine, diethylene triamine, triethylene tetramine, tetraethylene pentamine, pentaethylene hexamine, polyethylene imine, polyamide polyamine, and a combination thereof.

Epichlorohydrin, epibromohydrin, and α-methylepichlorohydrin may fall within the scope of the haloepoxy compound useful as a surface crosslinking agent. The mono-, di- or polyoxazolidinone compound may be exemplified by 2-oxazolidinone. Ethylene carbonate may be representative of the alkylene carbonate compound. These compounds may be used alone or in combination. In order to enhance the efficiency of the surface crosslinking process, the surface crosslinking agent preferably includes at least one polyhydric alcohol compound, and more preferably a polyhydric alcohol compound of 2 to 10 carbon atoms.

No limitations are imposed on the modality of adding the surface crosslinking agent to the superabsorbent base resin. For example, the surface crosslinking agent may be mixed with the superabsorbent base resin in a reactor, sprayed on the superabsorbent base resin, or fed, together with the superabsorbent base resin, into a reactor that continuously operates, such as a mixer.

The surface crosslinking modification may be conducted at 100 to 300° C. for 1 to 90 min. Within this relatively high temperature range, the surface crosslinking modification can be improved in efficiency, minimizing the content of remaining monomers in the final SAPs and providing excellent properties for the final SAPs. Throughout the specification, the temperature for surface crosslinking modification is defined as the overall temperature of the surface crosslinking agent and the polymer.

In the method of preparing surface-crosslinked superabsorbent polymers according to the present invention, a crosslinking reaction may be conducted for 1 to 90 min, and preferably for 5 to 60 min, after the temperature is elevated for the crosslinking reaction. A crosslinking reaction time of less than 1 min may not elicit a sufficient crosslinking reaction. On the other hand, when the crosslinking reaction time exceeds 90 min, excessive surface crosslinking may occur, degrading the physical properties of the SAPs somewhat and structurally destroying the SAP due to the lengthy retention in the reactor.

No particular limitations are imposed on the means for elevating the temperature for the surface crosslinking modification. For instance, a heat medium may be supplied, or direct heating may be performed using, e.g., electricity, but the present invention is not limited thereto. Examples of available heating sources include steam, electricity, UV light, IR light, and a heat medium.

In accordance with another aspect thereof, the present disclosure addresses a method for preparing a superabsorbent polymer for absorbing blood or highly viscous liquid, comprising:

a) providing a superabsorbent polymer;

b) pre-treating the superabsorbent polymer of step a) by mixing a water-soluble polyvalent cationic salt in an amount of 0.001 to 5.0 parts by weight, based on 100 parts by weight of the superabsorbent polymer provided in step a); and c) surface treating the pre-treated superabsorbent polymer of step b) by mixing a polycarbonic acid-based copolymer in an amount of 0.001 to 5.0 parts by weight, based on 100 parts by weight of the superabsorbent polymer provided in step a).

The method may further comprise classifying the surface-treated superabsorbent polymer by particle size into particles having sizes of less than 150 μm, from 150 μm to less than 300 μm, from 300 μm to less than 600 μm, from 600 μm to 850 μm, and greater than 850 μm.

The superabsorbent polymer may be a superabsorbent polymer product or a superabsorbent base resin.

The water-soluble polyvalent cationic salt plays a role in surface crosslinking in the superabsorbent polymer. In some embodiments, the water-soluble polyvalent cationic salt may be used in an amount of 0.001 to 5.0 parts by weight based on 100 parts by weight of the superabsorbent resin. Within this content range, the water-soluble polyvalent cationic salt can increase the permeability of the superabsorbent polymer without significantly degrading other properties.

In the water-soluble salt, the polyvalent cationic ion may be selected from the group consisting of $Al^{3+}$, $Zr^{4+}$, $Sc^{3+}$, $Ti^{4+}$, $V^{5+}$, $Cr^{3+}$, $Mn^{2+}$, $Fe^{3+}$, $Ni^{2+}$, $Cu^{2+}$, $Zn^{2+}$, $Ag^+$, $Pt^{4+}$, $Au^+$, and a combination thereof, while the counterpart anion may be selected from the group consisting of sulfate ($SO_4^{2-}$), sulfite ($SO_3^{2-}$), nitrate ($NO^{3-}$), metaphosphate ($PO^{3-}$), phosphate ($PO_4^{3-}$), and a combination thereof. The water-soluble salt may be particularly aluminum sulfate ($Al_2(SO_4)_3$), and more particularly zirconium sulfate ($Zr(SO_4)_2$), and may be in the form of a hydrate.

The polycarbonic acid-based copolymer may act as a superplasticizer in the superabsorbent polymer, and may have a structure in which a main chain is conjugated with a plurality of side chains or branches, like a comb, as shown in FIG. 3.

According to some embodiments, the polycarbonic acid-based copolymer consists of a main chain, having a (meth)acrylic acid-based monomer as a structural unit, and a side chain composed of an alkoxypolyalkylene glycol mono(meth)acrylic acid ester monomer. Preferably, the polycarbonic acid-based copolymer is contained in an amount of 0.001 to 5.0 parts by weight based on 100 parts by weight of the superabsorbent polymer. When used after treatment of the superabsorbent polymer with the water-soluble polyvalent cationic salt, the polycarbonic acid-based copolymer in this content range allows the superabsorbent polymer to improve in permeability while still retaining high processability, and without a significant degradation of other properties.

In a particular embodiment, the polycarbonic acid-based copolymer may contain 50 to 99% by weight of the alkoxypolyalkylene glycol mono(meth)acrylic acid ester monomer and 1 to 50% by weight of the (meth)acrylic acid monomer.

With the monomers in these ranges, the copolymer advantageously exhibits excellent dispersibility, slump retention, and initial dispersibility, along with appropriate air entrainment.

The alkoxypolyalkylene glycol mono(meth)acrylic acid ester monomer that serves as a side chain of the polycarbonic acid-based copolymer may be represented by the following Chemical Formula 1:

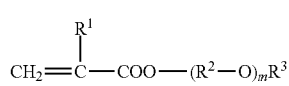

[Chemical Formula 1]

wherein, $R^1$ is a hydrogen atom or methyl;

$R^2O$ represents an oxyalkylene moiety of 2 to 4 carbon atoms;

$R^3$ is alkyl of 1 to 4 carbon atoms; and m is an integer of 50 to 200, expressing the average addition mole number of oxyalkylene.

When the average addition mole number of oxyalkylene ranges from 50 to 200, the side chain guarantees excellent dispersibility and slump retention. In a particular embodiment, the average addition mole number of oxyalkylene may be between 50 to 150.

The alkoxy polyalkylene glycol mono(meth)acrylic acid ester monomer may be at least one selected from the group consisting of methoxypolyethylene glycol mono(meth)acrylate, methoxypolypropylene glycol mono(meth)acrylate, methoxypolybutylene glycol mono(meth)acrylate, methoxypolyethylene glycol polypropylene glycol mono (meth)acrylate, methoxypolyethylene glycol polybutylene glycol mono(meth)acrylate, methoxypolypropylene glycol polybutylene glycol mono(meth)acrylate, methoxypolyethylene glycol polypropylene glycol polybutylene glycol mono(meth)acrylate, ethoxypolyethylene glycol mono (meth)acrylate, ethoxypolypropylene glycol mono(meth) acrylate, ethoxypolybutylene glycol mono(meth)acrylate, ethoxypolyethylene glycol polypropylene glycol mono (meth)acrylate, ethoxypolyethylene glycol polybutylene glycol mono(meth)acrylate, ethoxypolypropylene glycol polybutylene glycol mono(meth)acrylate, and ethoxypolyethylene glycol polypropylene glycol polybutylene glycol mono(meth)acrylate.

The (meth)acrylic acid monomer that serves as a structural unit of the main chain of the polycarbonic acid-based copolymer may be represented by the following Chemical Formula 2:

$R^2$—COO$M^1$      [Chemical Formula 2]

wherein, $R^2$ is an unsaturated hydrocarbon of 2 to 5 carbon atoms; and $M^1$ is a hydrogen atom, a monovalent or divalent metal, an ammonium group, or an organic amine group.

The (meth)acrylic acid monomer of Chemical Formula 2 may be at least one selected from the group consisting of an acrylic acid, a methacrylic acid, a monovalent or divalent metal salt thereof, an ammonium salt thereof, and an organic amine salt thereof.

The polycarbonic acid-based copolymer may be prepared by copolymerizing the monomers in the presence of a polymerization initiator. Copolymerization may be carried out by solution polymerization or bulk polymerization, but is not limited thereto.

For example, when polymerization is performed using water as a solvent, a water-soluble polymerization initiator, such as ammonium, alkali metal persulfate, or hydrogen peroxide, may be employed. Solution polymerization in a solvent such as a lower alcohol, an aromatic hydrocarbon, an aliphatic hydrocarbon, an ester compound or a ketone compound may employ as a polymerization initiator a peroxide, such as benzoylperoxide, lauroylperoxide, or cumen hydroperoxide, or an aromatic azo compound such as azobisisobutyronitrile. In this regard, an accelerator such as an amine compound may be used in combination therewith.

For polymerization in a water-lower alcohol mixture solvent, an eligible combination of the various polymerization initiators, and optionally the accelerator, may be used.

The polymerization initiator may be used in an amount of 0.5% to 5% by weight, based on the total weight of the monomer mixture, while the polymerization temperature may be set depending on the kind of the solvent or the polymerization initiator, and may range from 0° C. to 120° C.

In order to control the molecular weight of the polycarbonic acid-based copolymer, a thiol-based chain transfer agent may be added. The thiol-based chain transfer agent may be at least one selected from the group consisting of mercapto ethanol, thioglycerol, thioglycolic acid, 2-mercapto propionic acid, 3-mercapto propionic acid, thiomalic acid, thioglycolic acid octyl, and 3-mercapto propionic acid octyl, and may be used in an amount of 0.01% to 5% by weight, based on the total weight of the monomer mixture.

In a particular embodiment, the polycarbonic acid-based copolymer or a neutralized salt thereof may range in weight average molecular weight from 30,000 to 70,000, and preferably from 40,000 to 60,000 in consideration of dispersibility, as measured through GPC (Gel Permeation Chromatography).

According to some embodiments of the present disclosure, #427 polycarbonic acid-based copolymer, a novel polymer derived from the commercially available polycarbonic acid-based copolymer WRM 50 (LG Chem) by altering the side chain length and chain density thereof, is used for surface modification leading to an improvement in the properties thereof. For reference, #427 is identical to WRM50 with the exception that the molecular weight (length) of the alkoxypolyalkylene glycol mono(meth) acrylic acid ester monomer as a side chain is changed.

In Table 1, the polycarbonic acid-based copolymers WRM50, #426, and #427 are described for their basic properties including TSC (Total solid content: %), pH, and viscosity (25° C.), and results of GPC analysis are also listed. In addition, as shown in FIG. 3 and Table 2, the polycarbonic acid-based copolymers differ in structural features from one to another. The side chain alkoxypolyalkylene glycol mono(meth)acrylic acid ester monomer is longer (heavier) in #426 and #427 than WRM50, with a higher density of side chain for #427 than #426.

With regard to other descriptions of the SAPs of the preparation method according to the present disclosure, reference may be made to the SAPs for absorbing blood or highly viscous liquid according to the present disclosure.

MODE FOR INVENTION

A better understanding of the present disclosure may be obtained through the following examples that are set forth to illustrate, but are not to be construed as limiting the present disclosure. While specific embodiments of and examples for the invention are described above for illustrative purposes, various equivalent modifications are possible within the scope of the invention, as those skilled in the relevant art will recognize. In addition, unless stated otherwise, the terms "%" and "part", as used in the context of amount, are on the basis of mass.

Preparation of Hydrogel Phase Polymer, and Superabsorbent Polymer Production or Superabsorbent Base Resin A monomer mixture was obtained by mixing 100 g of acrylic acid, 0.3 g of polyethylene glycol diacrylate as a crosslinking agent, 0.033 g of diphenyl(2,4,6-trimethylbenzoyl)-phosphine oxide as an initiator, 38.9 g of caustic soda (NaOH), and 103.9 g of water. The monomer mixture was fed onto a continuously moving conveyer belt and subjected to polymerization for 2 min under UV light (intensity: 2 mW/cm$^2$) to obtain a hydrogel phase polymer. The hydrogel phase polymer obtained in Preparation Example 1 was cut into a size of 5×5 mm, dried for 2 hrs at 170° C. in a hot air drier, milled using a pin mill, and screened with a sieve to yield superabsorbent base resin particles with a size of 150 to 850 μm.

Preparation of Polycarbonic Acid-Based Copolymer #427

To a 2-L glass reactor equipped with a thermometer, a stirrer, a dropping funnel, a nitrogen inlet and a reflux condenser was added 200 parts by weight of water, and the reactor was purged with nitrogen gas and heated to 75° C. while the water was stirred.

After 20 parts by weight of an aqueous 3% by weight ammonium persulfate solution was added and slowly dissolved in the reactor, an aqueous monomer solution containing 400 parts by weight of methoxypolyethylene glycol monomethacrylate (average addition mole number of ethylene oxide of 100), 40 parts by weight of acrylic acid, 40 parts by weight of methacrylic acid, and 90 parts by weight of water, a mixture solution of 3.0 parts by weight of 2-mercapto ethanol and 30 parts by weight of water, and 70 parts by weight of an aqueous 3% by weight ammonium persulfate solution were dropwise added over 4 hrs. Thereafter, 10 parts by weight of an aqueous 3% by weight ammonium persulfate solution was added all at once. Then, the solution was maintained at 75° C. for 1 hr.

After the completion of polymerization, the reaction mixture was cooled to room temperature and neutralized for about 1 hr with an aqueous 30% by weight sodium hydroxide solution to afford a water-soluble copolymer salt having a solid content of 45%. The water-soluble copolymer salt was found to have a weight average molecular weight of 40,000, as measured by GPC (Gel Permeation Chromatography).

Preparation Example 1

In a high-speed mixer, 250 g of the superabsorbent polymer was mixed at 1000 rpm for 20 sec, and 6.25 g of a 25% by weight aqueous solution of $Al_2(SO_4)_3$(14-18 hydrate) (Junsei) was injected into the mixer through a plastic syringe, followed by mixing for an additional 3 min. Then, an 11% by weight aqueous solution of polycarbonic acid-based copolymer WRM50, #427, or #426 (LG Chem) was injected through a plastic syringe and mixed for an additional 3 min, and the high-speed mixer was slowly stopped. The resulting superabsorbent polymer was screened with a sieve to yield superabsorbent polymer particles with a size of 300 to 600 μm.

Preparation Example 2

In a high-speed mixer, 250 g of the superabsorbent polymer was mixed at 1000 rpm for 20 sec, and 6.25 g of a 25% by weight aqueous solution of $Al_2(SO_4)_3$(14-18 hydrate) was injected into the mixer through a plastic syringe, followed by mixing for an additional 3 min. After the high-speed mixer was slowly stopped, the resulting superabsorbent polymer was screened with a sieve to yield superabsorbent polymer particles with a size of 300 to 600 μm.

Preparation Example 3

In a high-speed mixer, 250 g of the superabsorbent polymer was mixed at 1000 rpm for 20 sec, and an 11% by weight aqueous solution of the polycarbonic acid-based copolymer WRM 50, #427, or #426 (LG Chem) was injected into the mixer through a plastic syringe, followed by mixing for an additional 3 min. After the high-speed mixer was slowly stopped, the resulting superabsorbent polymer was screened with a sieve to yield superabsorbent polymer particles with a size of 300 to 600 μm.

Examples 1 to 8 and Comparative Examples 1 to 9:
Preparation of Surface-Crosslinked SAPs Under the conditions listed in Table 3, below, SAPs of Examples 1 to 8 and Comparative Examples 1 to 9 were prepared.

TABLE 3

| | | SAP | Alum aq. Solution | | PCE aq. Solution | | | Preparation |
|---|---|---|---|---|---|---|---|---|
| | No. | (250 g) | $Al_2(SO_4)_2$•14-18$H_2O$ | $H_2O$ | PCE Name | PCE Amount (g) | $H_2O$ (g) | Ex. |
| #1 | C. Ex. 1 | Product | — | — | None | — | — | — |
| #2 | C. Ex. 2 | | 1.5625 | 4.6875 | | | — | 2 |
| #3 | C. Ex. 3 | | — | — | WRM50 | 0.827 | 6.673 | 3 |
| #4 | C. Ex. 4 | | | | | 1.654 | 13.346 | |
| #5 | Ex. 1 | | 1.5625 | 4.6875 | | 0.827 | 6.673 | 1 |
| #6 | Ex. 2 | | | | | 1.654 | 13.346 | |
| #7 | C. Ex. 5 | | — | — | #426 | 0.827 | 6.673 | 3 |
| #8 | C. Ex. 6 | | | | | 1.654 | 13.346 | |
| #9 | Ex. 3 | | 1.5625 | 4.6875 | | 0.827 | 6.673 | 1 |
| #10 | Ex. 4 | | | | | 1.654 | 13.346 | |

TABLE 3-continued

| No. | SAP (250 g) | Alum aq. Solution Al$_2$(SO$_4$)$_2$·14-18H$_2$O | H$_2$O | PCE aq. Solution PCE Name | PCE Amount (g) | H$_2$O (g) | Preparation Ex. |
|---|---|---|---|---|---|---|---|
| #11 | C. Ex. 7 | — | — | #427 | 0.827 | 6.673 | 3 |
| #12 | C. Ex. 8 | | | | 1.654 | 13.346 | |
| #13 | Ex. 5 | 1.5625 | 4.6875 | | 0.827 | 6.673 | 1 |
| #14 | Ex. 6 | | | | 1.654 | 13.346 | |
| #15 | C. Ex. 9 | Base | — | — | None | — | — | — |
| #16 | Ex. 7 | Resin | 1.5625 | 4.6875 | #427 | 1.654 | 6.673 | 1 |
| #17 | Ex. 8 | | | | | 3.75 | 13.346 | |

Test Example: Assay for Physical Properties of SAPs (Blood Fluidity of SAPs Surface-Modified with Alum and Polycarbonic Acid-Based Copolymer)

Blood Test

After weighing, a glass petri dish with an internal diameter of 3 cm was sprinkled with 1 g of superabsorbent polymer particles having a size of 300~600 μm, and tapped on the bottom thereof so as to evenly distribute the particles. Then, 0.1 ml of sheep's blood was continuously added dropwise to the center of the superabsorbent polymer particles through a 1 mL plastic syringe with a 21 G needle, followed by allowing the blood to clot at room temperature for 2 hrs. The clear superabsorbent polymer particles that did not coagulate with the clotted blood were removed before the glass petri dish was weighed to calculate the weight of the superabsorbent polymer coagulated with blood.

TABLE 4

Spreadability of Blood over SAPs Treated with Alum and PCE

| No. | | Blood Test Result (mg) |
|---|---|---|
| #1 | C. Example 1 | 89.7 |
| #2 | C. Example 2 | 42.7 |
| #3 | C. Example 3 | 73.9 |
| #4 | C. Example 4 | 72.8 |
| #5 | Example 1 | 108.7 |
| #6 | Example 3 | 108.5 |
| #7 | C. Example 5 | 71.6 |
| #8 | C. Example 6 | 89.6 |
| #9 | Example 3 | 100.6 |
| #10 | Example 4 | 123.8 |
| #11 | C. Example 7 | 80.4 |
| #12 | C. Example 8 | 103.3 |
| #13 | Example 5 | 119.4 |
| #14 | Example 6 | 134.2 |
| #15 | C. Example 9 | 61.8 |
| #16 | Example 7 | 165.1 |
| #17 | Example 8 | 178.7 |

Figure 1:
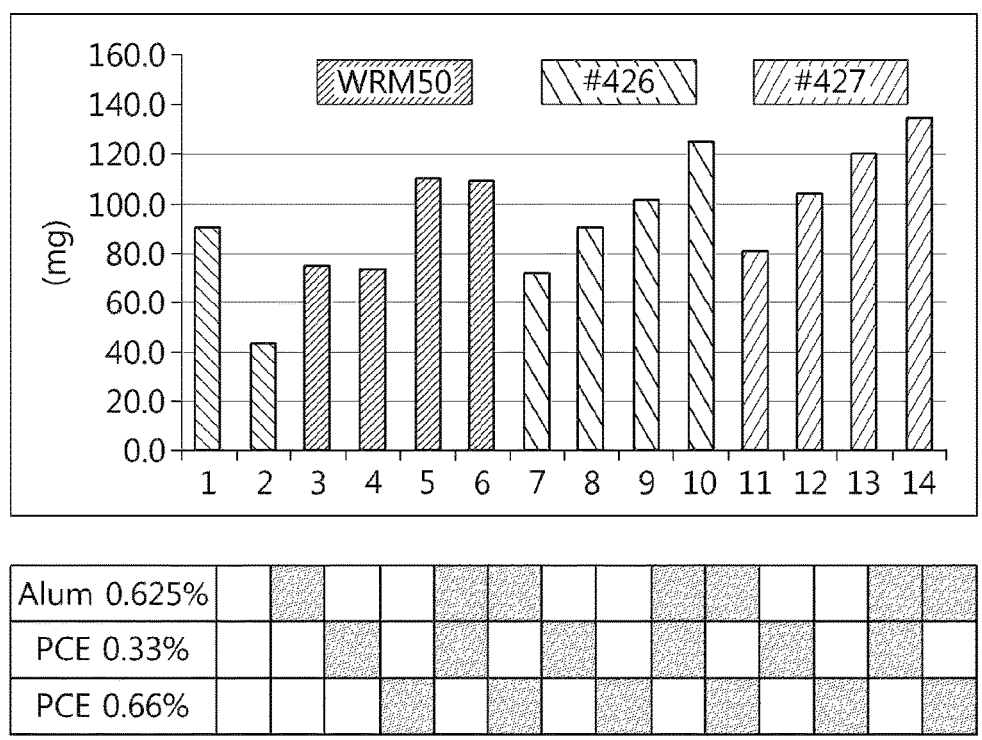
FIG. 1 is a graph showing blood fluidity changes in SAPs according to the use of polyvalent cationic salts and the kind and concentration of polycarbonic acid-based copolymers (Comparative Example 1, Comparative Example 2, Comparative Example 3, Comparative Example 4, Example 1, Example 2, Comparative Example 5, Comparative Example 6, Example 3, Example 4, Comparative Example 7, Comparative Example 8, Example 5, Example 6, Comparative Example 9, Example 7, and Example 8 from the left to the right).
Figure 2:
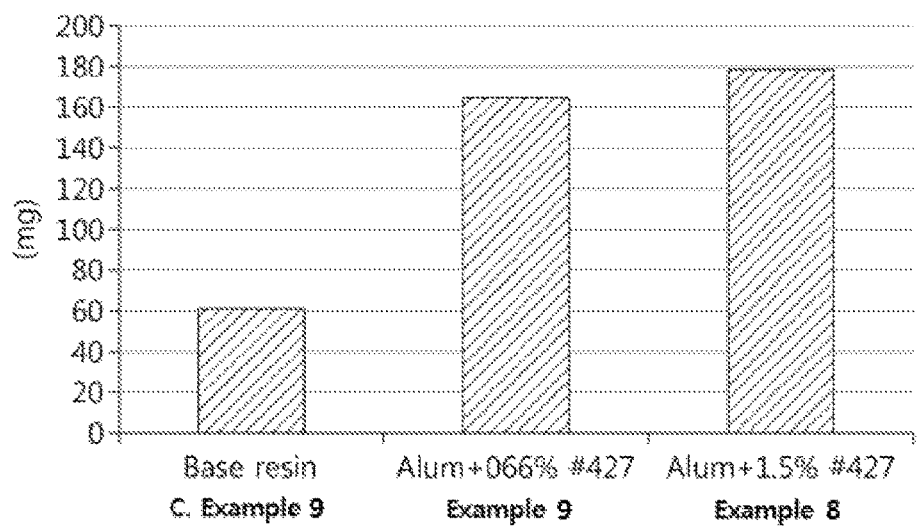
FIG. 2 is a graph showing blood fluidity changes in superabsorbent base resins according to concentrations of the polycarbonic acid-based copolymer #427.

As can be seen in Table 4 and FIGS. 1 and 2, the superabsorbent polymer surface-treated with a polycarbonic acid-based copolymer absorbed more blood and more thoroughly dispersed blood drops therein. The spreading of blood was remarkably improved in the superabsorbent polymers that were pre-treated with Al$_2$(SO$_4$)$_3$ and then with a polycarbonic acid-based copolymer, compared to those treated with either Al$_2$(SO$_4$)$_3$ or a polycarbonic acid-based copolymer. Moreover, better blood fluidity was detected with longer branches of the polycarbonic acid-based copolymer and a higher density of the branches. In addition, a polycarbonic acid-based copolymer concentration of 0.66% elicited higher blood fluidity, compared to 0.33%.

From the data on the blood fluidity of SAPs, obtained according to the use of polyvalent cationic salts and the kind and concentration of polycarbonic acid-based copolymers, the SAPs for absorbing blood or highly viscous liquid in accordance with the present disclosure are proven to exhibit excellent blood fluidity as analyzed by the new assay, proposed by the present disclosure, for measuring the weight of a superabsorbent polymer coagulated with blood or highly viscous liquid clots. Particularly, the use of a superabsorbent base resin ensures a great improvement in physical properties, and increases blood fluidity by 30 mg between pre- or post-surface modification. Exhibiting high blood fluidity, therefore, the SAPs of the present disclosure therefore can find applications in sanitary pads for absorbing blood or highly viscous liquid.

The invention claimed is:

1. A superabsorbent polymer for absorbing blood or highly viscous liquid, prepared by subjecting a superabsorbent resin to surface modification with a water-soluble polyvalent cationic salt and a polycarbonic acid-based copolymer.

2. The superabsorbent polymer of claim 1, wherein the superabsorbent resin is a superabsorbent polymer product or a superabsorbent base resin.

3. The superabsorbent polymer of claim 1, wherein the water-soluble polyvalent cationic salt is contained in an amount of 0.001 to 5.0 parts by weight based on 100 parts by weight of the superabsorbent resin.

4. The superabsorbent polymer of claim 1, wherein the water-soluble polyvalent cationic salt comprises a cationic ion selected from the group consisting of $Al^{3+}$, $Zr^{4+}$, $Sc^{3+}$, $Ti^{4+}$, $V^{5+}$, $Cr^{3+}$, $Mn^{2+}$, $Fe^{3+}$, $Ni^{2+}$, $Cu^{2+}$, $Zn^{2+}$, $Ag^+$, $Pt^{4+}$, $Au^+$, and a combination thereof, and an anion selected from the group consisting of sulfate ($SO_4^{2-}$), sulfite ($SO_3^{2-}$), nitrate ($NO^{3-}$), metaphosphate ($PO^{3-}$), phosphate ($PO_4^{3-}$), and a combination thereof.

5. The superabsorbent polymer of claim 4, wherein the water-soluble polyvalent cationic salt is aluminum sulfate ($Al_2(SO_4)_3$) or zirconium sulfate ($Zr(SO_4)_2$).

6. The superabsorbent polymer of claim 1, wherein the polycarbonic acid-based copolymer is contained in an amount of 0.001 to 5.0 parts by weight based on 100 parts by weight of the superabsorbent polymer.

7. The superabsorbent polymer of claim 6, wherein the polycarbonic acid-based copolymer is contained in an amount of 0.001 to 3.0 parts by weight based on 100 parts by weight of the superabsorbent polymer.

8. The superabsorbent polymer of claim 1, wherein the polycarbonic acid-based copolymer is prepared by copolymerizing an alkoxypolyalkylene glycol mono(meth)acrylic acid ester monomer with a (meth)acrylic acid monomer.

9. The superabsorbent polymer of claim 8, wherein the alkoxypolyalkylene glycol mono(meth)acrylic acid ester monomer is represented by the following Chemical Formula 1:

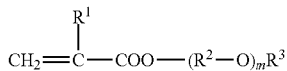   [Chemical Formula 1]

wherein, $R^1$ is a hydrogen atom or methyl;

$R^2O$ represents an oxyalkylene moiety of 2 to 4 carbon atoms;

$R^3$ is alkyl of 1 to 4 carbon atoms; and m is an integer of 50 to 200, expressing an average addition mole number of oxyalkylene.

10. The superabsorbent polymer of claim 8, wherein the alkoxypolyalkylene glycol mono(meth)acrylic acid ester monomer is at least one selected from the group consisting of methoxypolyethylene glycol mono(meth)acrylate, methoxypolypropylene glycol mono(meth)acrylate, methoxypolybutylene glycol mono(meth)acrylate, methoxypolyethylene glycol polypropylene glycol mono (meth)acrylate, methoxypolyethylene glycol polybutylene glycol mono(meth)acrylate, methoxypolypropylene glycol polybutylene glycol mono(meth)acrylate, methoxypolyethylene glycol polypropylene glycol polybutylene glycol mono(meth)acrylate, ethoxypolyethylene glycol mono (meth)acrylate, ethoxypolypropylene glycol mono(meth) acrylate, ethoxypolybutylene glycol mono(meth)acrylate, ethoxypolyethylene glycol polypropylene glycol mono (meth)acrylate, ethoxypolyethylene glycol polybutylene glycol mono(meth)acrylate, ethoxypolypropylene glycol polybutylene glycol mono(meth)acrylate, and ethoxypolyethylene glycol polypropylene glycol polybutylene glycol mono(meth)acrylate.

11. The superabsorbent polymer of claim 8, wherein the (meth)acrylic acid monomer is represented by the following Chemical Formula 2:

$R^2$—$COOM^1$   [Chemical Formula 2]

wherein, $R^2$ is an unsaturated hydrocarbon of 2 to 5 carbon atoms; and $M^1$ is a hydrogen atom, a monovalent or divalent metal, an ammonium group, or an organic amine group.

12. The superabsorbent polymer of claim 8, wherein the (meth)acrylic acid monomer is at least one selected from the group consisting of an acrylic acid, a methacrylic acid, a monovalent or divalent metal salt thereof, an ammonium salt thereof, and an organic amine salt thereof.

13. The superabsorbent polymer of claim 1, wherein the absorption of blood or highly viscous liquid by the superabsorbent polymer is assayed by a blood test in which a weight of the superabsorbent polymer, coagulated with blood, is measured when 0.1 ml of blood is applied per gram of the superabsorbent polymer.

14. The superabsorbent polymer of claim 13, wherein the blood test is carried out by adding blood dropwise onto the superabsorbent polymer, allowing the blood to clot, and calculating the weight of the superabsorbent polymer coagulated with the clotted blood to express blood fluidity.

* * * * *